(12) United States Patent
Py

(10) Patent No.: US 6,213,982 B1
(45) Date of Patent: Apr. 10, 2001

(54) ONE-WAY ACTUATION RELEASE MECHANISM FOR A SYSTEM FOR APPLYING MEDICAMENT

(76) Inventor: Daniel Py, 8 Normandy Rd., Larchmont, NY (US) 10538

( * ) Notice: Subject to any disclaimer, the term of this patent is extended or adjusted under 35 U.S.C. 154(b) by 0 days.

(21) Appl. No.: 09/478,432

(22) Filed: Jan. 6, 2000

Related U.S. Application Data

(63) Continuation of application No. 08/993,969, filed on Dec. 18, 1997, now Pat. No. 6,033,384.

(51) Int. Cl.$^7$ .................................................... A61M 5/178
(52) U.S. Cl. ............................ 604/186; 604/153; 222/210
(58) Field of Search ................................. 604/185, 186, 604/216, 217, 249, 257, 212, 226, 227, 290, 142, 153, 521, 519; 222/207, 209, 210, 211, 221.1, 221.7

(56) References Cited

U.S. PATENT DOCUMENTS

| | | | |
|---|---|---|---|
| 4,575,375 | * | 3/1986 | Kozam .................................. 604/185 |
| 5,205,441 | * | 4/1993 | Adris .................................... 222/207 |
| 5,238,845 | * | 8/1993 | Adris .................................... 222/207 |

* cited by examiner

Primary Examiner—Anhtuan T. Nguyen
(74) Attorney, Agent, or Firm—Kenyon & Kenyon

(57) ABSTRACT

A medicament-dispensing system includes a cartridge for housing and actuating an accordion-like vial-dispenser for dispensing a calibrated amount of medicament by means of a single actuation motion which sequentially loads the vial-dispenser and dispenses the loaded medicament. The vial-dispenser has a front bellows portion, a rear bellows portion, an internal piston mechanism, a medicament storage chamber and a dosage cavity. The cartridge has a trigger mechanism which acts in concert with a notched lever and a wedge-shaped arm internally located in the cartridge to sequentially load the dosage cavity with medicament and discharge it. Depression of the trigger mechanism simultaneously extends, by means of the notched lever, the front bellows portion and compresses the rear bellows portion to load the dosage cavity with medicament. Once the notched lever has extended the front bellows portion a predetermined distance, the notched lever is disengaged from the front bellows portion by the wedge-shaped arm extending from the rear wall of the housing, thereby releasing the front and rear bellows portions, along with the internal piston mechanism, to return to original position and force the medicament from the dosage cavity via a nozzle of the vial-dispenser.

11 Claims, 4 Drawing Sheets though to be released under normal # ONE-WAY ACTUATION RELEASE MECHANISM FOR A SYSTEM FOR APPLYING MEDICAMENT This application is a continuation of prior application Ser. No. 08/993,969, filed Dec. 18, 1997, now U.S. Pat. No. 6,033,384.

BACKGROUND OF THE INVENTION

1. Field of the Invention

The invention relates generally to a mechanism for dispensing medicament via an outlet nozzle, and relates more particularly to a one-way actuation release mechanism for a medicament dispensing system for applying medicament from a vial-dispenser of the type which is actuated by compression or movement of a trigger.

2. Description of Related Art

Amongst various dispensers for applying medicament, a typical medicament container includes a flexible vial storage portion and a nozzle for dispensing medicament by squeezing the vial between its side walls. Another type of medicament dispenser is an accordion-like or piston-like dispenser which is actuated by squeezing the vial between a bottom wall and the nozzle so as to compress the vial in its longitudinal direction, rather than from its sides. The present invention is particularly directed to a dispensing system which includes such an accordion-like or piston-like dispenser, although the present invention may be used in conjunction with other types of dispensers. An example of the piston-like dispenser which ejects precalibrated dosage of medicament is described in detail in my U.S. Pat. No. 5,613,957 which is expressly incorporated herein by reference.

Normally, several factors contribute to difficulty in applying medicament. First, elderly people often encounter difficulty in holding the dispenser steady or squeezing the dispenser to apply a proper quantity of medicament. In addition, even for young persons who are able to hold the dispenser steady, actuation of certain types of dispensers creates problems in accurate application of medicament. For example, application of medicament using a common type of nasal dispenser requires initial placement of the nozzle tip inside the nostril, followed by withdrawal of the nozzle tip from the nostril due to the compression of the dispenser at the time of ejection of medicament, which may result in accidental application of medicament to the eyes or other unintended targets.

Even if the medicament is properly applied as intended, typically the dispensed dose of medicament will vary with the speed and/or the force of actuation of the pump mechanism. In addition, the spray pattern, or the plume, of the dispensed medicament will also vary with the speed and/or the force of actuation of the pump mechanism.

Yet another problem associated with medicament dispensers is manufacturing complexity: pump-type medicament dispensers are currently made of numerous parts and are highly delicate to assemble. Many of the pump-type dispensers incorporate springs, which pose problems in the manufacturing process for the dispensers because of the springs' tendency to get intermingled.

One attempt to solve the above-described problems associated with applying medicament from a dispenser is described in my U.S. Pat. No. 5,267,986, which discloses a system including a cartridge for actuating a piston-like or accordion-like vial-dispenser for applying medicament to an eye. The cartridge disclosed in U.S. Pat. No. 5,267,986 includes: a housing for holding the vial-dispenser; a telescoping cylinder for compressing the vial-dispenser in the longitudinal direction to load the vial with medicament; a locking mechanism for locking the telescoping cylinder and the vial-dispenser in the loaded position, against the urging of a spring mechanism of the vial-dispenser; and a trigger mechanism for releasing the telescoping cylinder and the vial-dispenser from the locked position to release the medicament loaded in the dispenser by means of the force of the spring mechanism. In order to obviate the need for a discrete spring element in the pump mechanism of the vial-dispenser, a portion of the vial-dispenser body is made of an elastic material which is compressible and provides spring force. The two-step process in which the cartridge disclosed in U.S. Pat. No. 5,267,986 loads and subsequently releases the medicament from a vial-dispenser defines the basic operation a "reverse pump," an example of which is described in U.S. Pat. No. 5,613,957.

The dispensing system disclosed in U.S. Pat. No. 5,267,986 addresses the previously-mentioned problems by enabling a user to apply a predetermined dose of medicament independent of the physical force applied to the dispensing system by the user: the releasing force or speed of the dispensed medicament is dependent on the integral spring element of the dispensing system. Whereas conventional pump-type dispensers often utilize compression along the longitudinal axis for release of medicament, the actuation motion of the release mechanism described in U.S. Pat. No. 5,267,986 is preferably achieved in a direction perpendicular to the longitudinal axis of the vial-dispenser to ensure enhanced leverage for the user.

Because elastic materials, particularly elastomeric materials and springs, tend to exhibit hysteresis, spring force decreases if the spring mechanism is kept in the compressed position, i.e., in the loaded, locked position. Although the deformation of spring is generally reversible if the spring is returned to, and maintained in, the unbiased state for some period, some of the deformation becomes irreversible, or experiences "creep," if the spring is kept in the compressed state beyond a certain threshold period of time, which threshold period varies with the spring material. The amount of loss of spring force is dependent on the tendency of a particular spring material to "creep," and it is known that metal springs tend to exhibit much less "creep," than plastic springs. The hysteresis of elastic materials used to form the spring mechanism of the pump described in U.S. Pat. 5,613,957 is due to loss of some of the spring property when the spring element remains in the compressed state for an extended period of time.

Two examples illustrate the practical implications of the above-mentioned hysteresis problem-in connection with the dispensing system disclosed in U.S. Pat. No. 5,267,986. As a first example, a user places the dispensing system in the loaded state but does not actuate the release mechanism for several minutes due to an interruption. When the release mechanism is finally actuated, hysteresis of the spring mechanism causes the dosage of released medicament to vary from the dosage calibrated to be released under normal conditions. As a second example, a user places the dispensing system in the loaded state but subsequently forgets about the loaded system; the user does not actuate the release mechanism for several weeks or months. In this situation, not only will the initially-released dosage vary from the calibrated dosage, but subsequently-dispensed dosages will also vary from the calibrated dosage due to a type of permanent deformation, or "creep," that has occurred.

In view of the above-described problem of spring deformation, it would be desirable to have a medicament-dispensing system which allows the user, by means of a single actuation motion, to load the vial with medicament and dispense the medicament.

SUMMARY OF THE INVENTION

It is an object of the invention to provide a medicament-dispensing system which can accurately deliver a small, calibrated amount of medicament by means of a single actuation motion which initially loads the system with medicament and subsequently dispenses the loaded medicament.

It is a further object of the invention to provide such a system which includes an actuation mechanism for actuating a vial-dispenser of the type having a spring configuration, e.g., an accordion-like or piston-like vial-dispenser, which actuation mechanism requires minimal force for actuation.

It is a further object of the invention to provide such a system which substantially eliminates any possibility that spring elements of the dispensing system will exhibit hysteresis of spring characteristics.

It is a further object of the invention to provide such a system which ensures that the discharged dosages do not substantially deviate from the calibrated dosage.

It is a further object of the invention to provide such a system in which the actuation motion of the actuation mechanism for dispensing the loaded medicament is in the direction perpendicular to the longitudinal axis of the vial dispenser to ensure enhanced leverage for the user and to avoid the actuation motion being parallel to the compression axis of the spring element.

It is a further object of the invention to provide such a system which can accurately deliver a small, calibrated amount of medicament in a stable manner independent of the physical force applied by the user to the actuation mechanism.

It is a further object of the invention to provide a system having these features which has a simple construction and which is easy to manufacture by virtue of reduced number of components, particularly by virtue of eliminating the need for a discrete spring element.

It is a further object of the invention to provide a method of accurately delivering a small, calibrated amount of medicament by means of a single actuation motion of a medicament-dispensing system which initially loads the system with medicament and subsequently dispenses the loaded medicament.

It is a further object of the invention to provide a method of dispensing a small, calibrated amount of medicament by means of an actuation mechanism for actuating an accordion-like or piston-like vial-dispenser, which actuation motion requires minimal force for actuation.

The foregoing objects are achieved by the present invention which provides a medicament-dispensing system in which a cartridge or housing is particularly adapted for actuating an accordion-like or piston-like vial-dispenser. The vial-dispenser has an accordion-like front bellows portion near the anterior end, a rear vial section or liquid storage chamber at the posterior end, and a rear bellows portion located between the front bellows portion and the rear vial section. A drop cavity or a dosage cavity, which may be located within either the front bellows portion or the rear bellows portion, holds a precalibrated amount of medicament loaded from the liquid storage chamber. In addition, an internal piston mechanism within the vial-dispenser acts in concert with the front and rear bellows portions to expel the medicament contained in the drop cavity.

The housing includes a generally elongated body portion which is adapted to receive the vial-dispenser between an anterior wall and a posterior wall of the housing. The posterior wall of the housing may form a portion of a rear chamber of the housing, in which case the rear chamber of the housing receives the rear vial section of the vial-dispenser. The anterior wall of the housing has an aperture for exposing the nozzle of the vial. The nozzle is preferably receded within the anterior portion of the housing so that it does not project out of the opening so as to prevent any corneal injury in the event of accidental contact of the anterior portion with the eye.

Located on top portion of the housing is a hook-shaped trigger mechanism which, when depressed, acts via, and in concert with, a notched lever located in the interior portion of the housing to extend the front bellows portion and compress the rear bellows portion of the vial-dispenser in the longitudinal direction, away from the anterior wall of the housing and towards the rear chamber. In the case of the exemplary embodiment of the vial-dispenser described herein, extension of the front bellows portion and compression of the rear bellows portion cause a precalibrated dose of medicament to enter the dosage cavity located in the front of the dispenser, thereby "loading" the dosage cavity.

Continuing with the triggering motion, once the notched lever located in the interior portion of the housing has extended the front bellows portion of the vial-dispenser a predetermined distance, the notched lever is disengaged from the front bellows portion by a wedge-shaped arm extending from the rear wall of the housing. Upon disengagement from the notched lever, the front bellows portion contracts and the rear bellows portion extends towards the anterior wall of the housing. In concert with the movements of the front and rear bellows portions, movement of the internal piston mechanism creates pressure which forces the medicament from the dosage cavity via the anterior nozzle of the vial-dispenser.

DETAILED DESCRIPTION OF THE INVENTION

Figure 1:
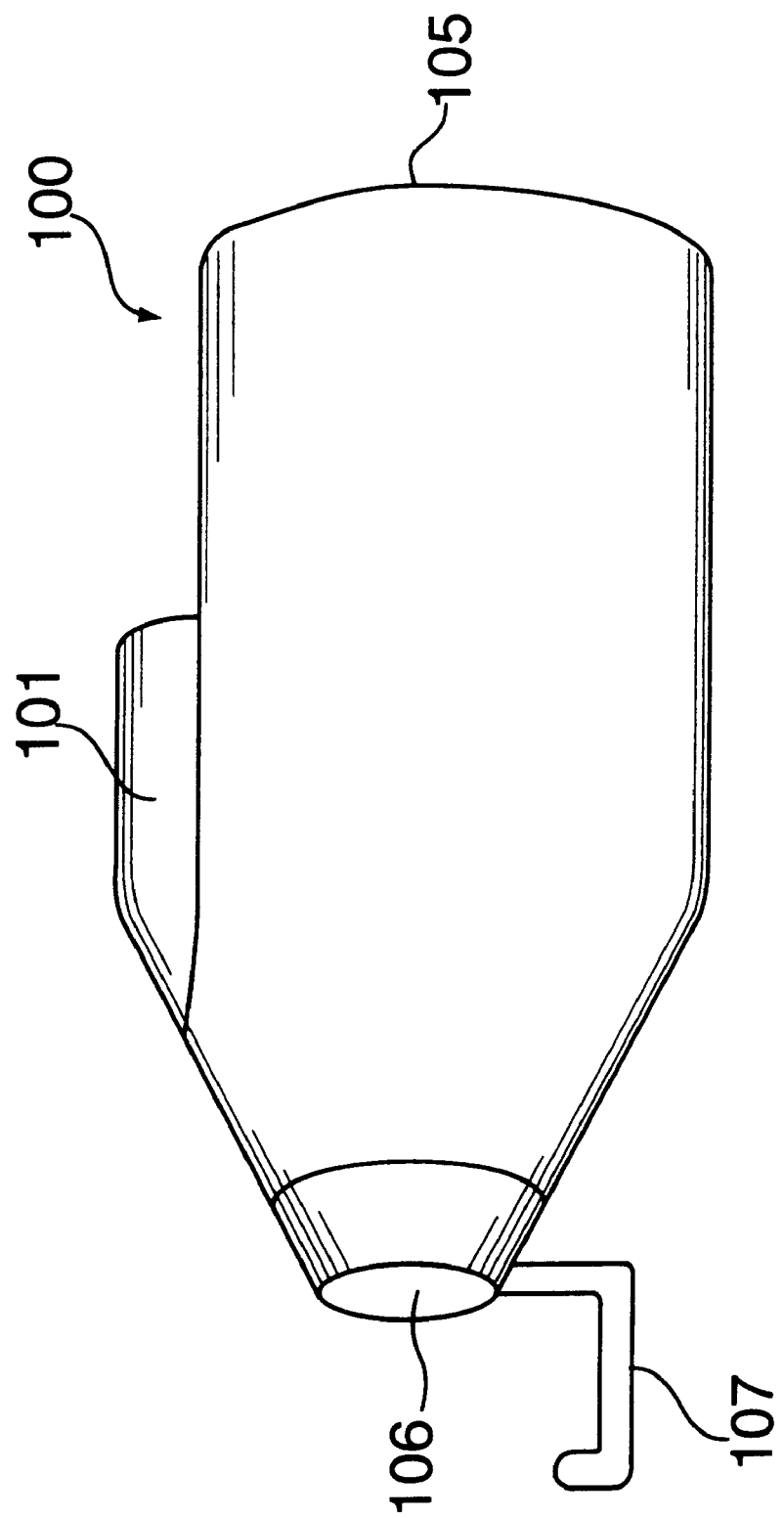
FIG. 1 is a perspective view of a housing of a dispensing system in accordance with the present invention.
Figure 2:
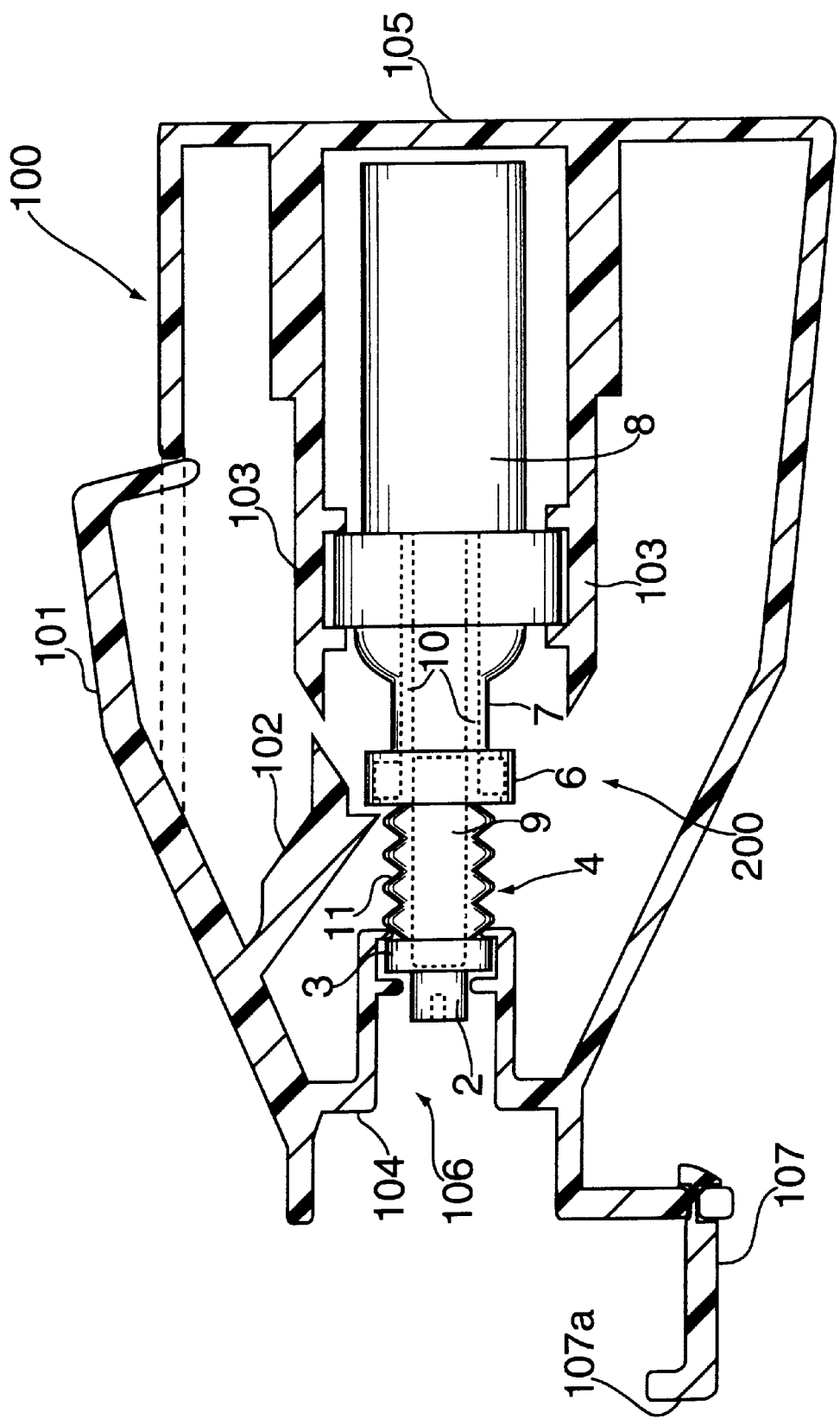
FIG. 2 is a detailed cross-sectional side view of a the dispensing system including the housing and the vial-dispenser in accordance with the present invention, which dispensing system is shown in a rest position.
Figure 3:
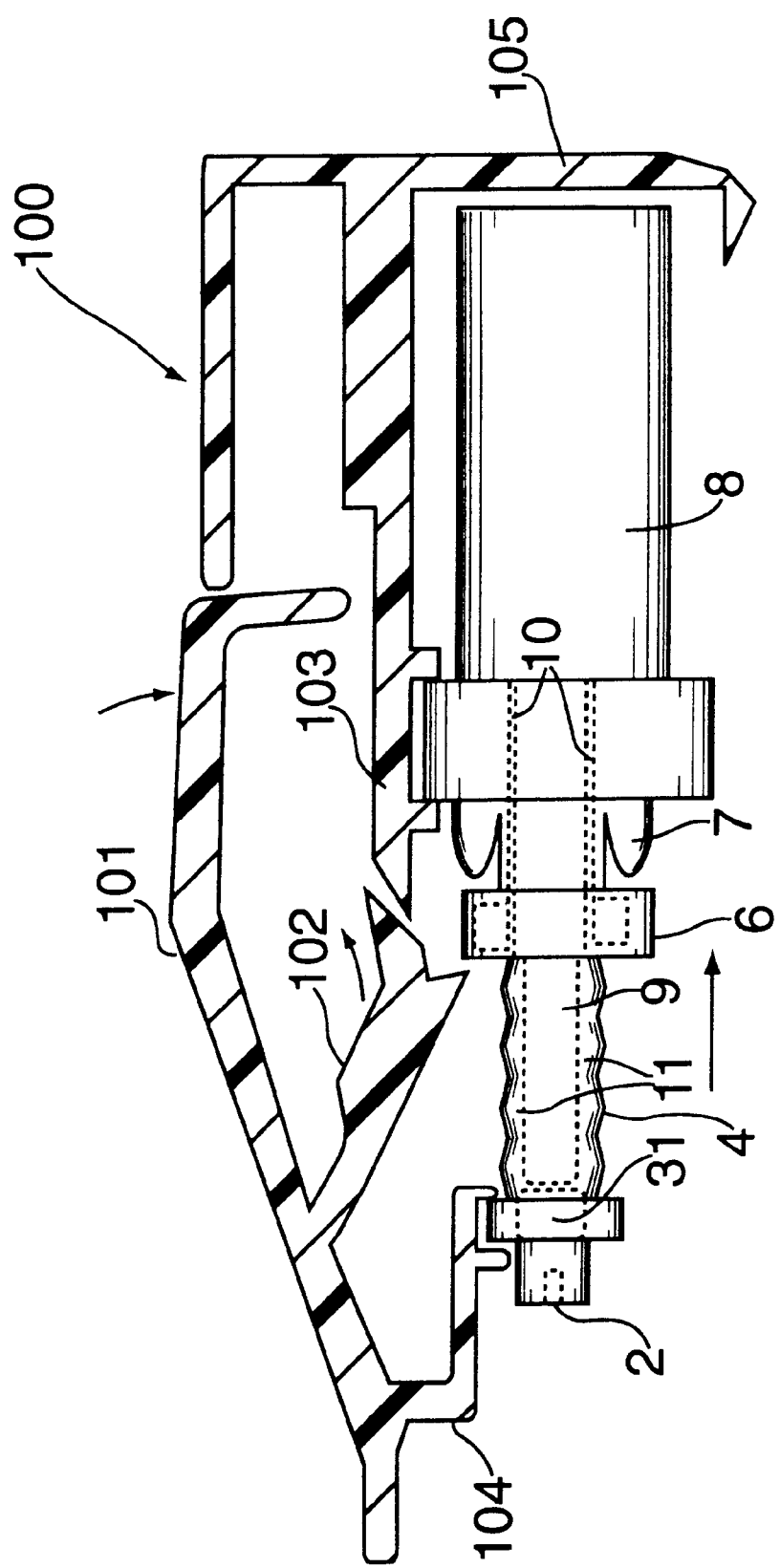
FIG. 3 is a detailed cross-sectional side view of the dispensing system including the housing and the vial-dispenser in accordance with the present invention, which dispensing system is shown in an intermediate position during actuation of the trigger mechanism.
Figure 4:
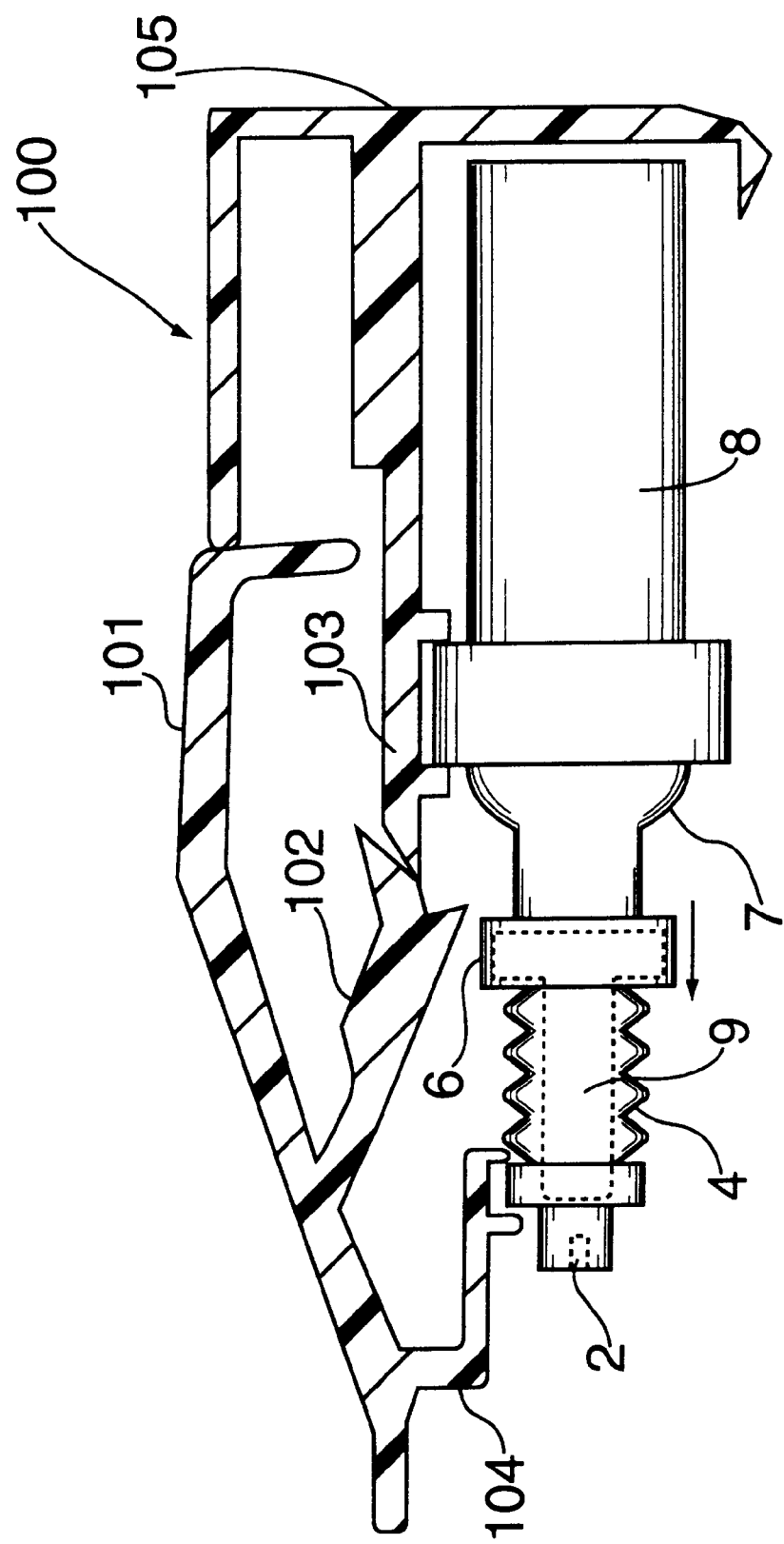
FIG. 4 is a detailed cross-sectional side view of the dispensing system including the housing and the vial-dispenser in accordance with the present invention, which dispensing system is shown in a release position during actuation of the trigger mechanism.

The medicament-dispensing system according to the present invention includes a housing or cartridge 100, shown in FIG. 1, which is adapted to house and work in conjunction with an accordion-like or piston-like vial-dispenser 200, shown in FIGS. 2–4. Although the present invention is described in conjunction with the vial-dispenser shown in FIGS. 2–4, the present invention is not limited to this particular dispenser.

As shown in FIG. 2, the vial-dispenser generally depicted at 200 includes a nozzle 2, a front wing 3, a front bellows portion 4, a rear wing 6, a rear bellows portion 7 and a rear vial section or liquid storage chamber 8 containing a storage supply of liquid medicament. The vial-dispenser 200 is compressible in the longitudinal direction along the bellows. For this purpose, the front and rear bellows portions 4 and 7, respectively, are constructed of a soft flexible plastic material such as the thermoplastic resin sold under the name Kraton from the Shell Company. Resiliency of the dispenser is provided by the spring action of the front and rear bellows made of Kraton, which has an excellent memory and serves as an excellent spring.

As shown in FIG. 3, the vial-dispenser 200 further includes a drop cavity, or dosage cavity, 31 therein which holds, when the dispensing system is activated, a predetermined volume of fluid to be emitted through the nozzle 2. In addition, a pump piston 9 within the vial-dispenser is anchored to the rear wing 6 such that the piston 9 moves in unison with the rear wing 6. Furthermore, as shown in FIGS. 2 and 3, conduit channels 10, which connect the rear vial section 8 to the front bellows portion 4, and circumferential channels 11 within the front bellows portion 4, are provided to serve as conduits for supplying medicament to the drop cavity 31 upon actuation of the dispensing system. As will be described in further detail below, a single actuation motion of the trigger mechanism of the dispensing system sequentially accomplishes filling, or loading, of the drop cavity with medicament from the rear vial section 8, and subsequent discharge of the medicament from the drop cavity via the nozzle 2.

As shown in FIGS. 1 and 2, the cartridge or housing 100 of the dispensing system according to the present invention has a generally cylindrical shape, although any other convenient shape for handling may be employed. The housing 100 includes an anterior wall 104 which has a centrally located aperture 106 for the discharge of medicament from the nozzle 2, a posterior wall 105, wedge-shaped arms 103 which extend internally from the posterior wall 105, a trigger 101 and an internal notched lever 102 which acts in concert with the trigger 101.

As shown in FIG. 2, the vial-dispenser 200 is positioned within the housing 100 such that in resting position the front wing 3 rests against the anterior wall 104, the rear vial section 8 rests against the posterior wall 105, and the notched lever 102 engages the rear wing 6. Preferably, the housing 100 is dimensioned such that the dispenser 200 can fit snugly within the housing, with the nozzle 2 completely receded within the aperture 106 of the anterior wall 104, thereby preventing accidental contact of the nozzle 2 with the eye, as well as preventing contamination of the outside of the nozzle. In addition, the posterior wall 105 may form, in conjunction with the wedge-shaped arms 103, a rear chamber for accommodating the rear vial section 8.

From the rest position illustrated in FIG. 2, the dispensing system according to the present invention is actuated by depressing the trigger 101. In concert with the depression of trigger 101, the notched lever 102 moves laterally towards the posterior wall 105 while engaged to the rear wing 6, thereby extending the front bellows portion 4 and compressing the rear bellows portion 7 along the longitudinal axis of the vial-dispenser 200, as shown in FIG. 3. As can be seen from FIGS. 2 and 3, when the front bellows portion is extended by the notched lever 102 which is engaged to the rear wing 6, the internal pump piston 9 is also moved laterally towards the posterior wall 105. The combined movement of the front bellows 4, the pump piston 9 and the rear bellows 7 causes drop in pressure in the drop cavity 31, and the drop cavity is filled, or "loaded," with medicament channeled from the rear vial section 8 via the conduit channels 10 and circumferential channels 11.

Continuing with the actuation sequence, further depression of the trigger 101 causes the notched lever 102 to eventually reach a position where the notched lever comes in contact with the wedge-shaped arm 103. At this point, the wedge-shaped arm engages the notched lever 102 and lifts the notched lever clear of the rear wing 6, as shown in FIG. 4. Upon release from the notched lever 102, the spring action of the front bellows portion 4 and the rear bellows portion 7 causes the rear wing 6 and the pump piston 9 to move towards the anterior wall 104, as shown in FIG. 4. The movement of the pump piston 9 creates pressure which forces the medicament to be discharged from the drop cavity 31 via the nozzle 2. Subsequently, when the trigger 101 is released, the notched lever 102 is disengaged from the wedge-shaped arm 103, and the spring action of the notched lever 102 allows the notched lever to snap back into the resting position shown in FIG. 2.

If the medicament dispensing system according to the present invention is to be used for application of medicament to the eyes, the lower anterior section of housing 100 may be additionally equipped with a forwardly projecting finger 107 which extends from the housing 100 beyond the anterior wall 104, as shown in FIGS. 1 and 2. The finger 107 is upwardly curved to define a smooth surface 107a for engaging the lower eyelid and preferably covered with a soft sleeve. The finger is preferably coated with a material such as Kraton. It should be noted, however, that the forwardly projecting finger 107 is entirely optional even for application of medicament to the eyes. Of course, for uses other than application of medicament to the eyes, practical considerations will dictate whether the forwardly projecting finger 107 should be modified or even entirely omitted from the lower anterior section of the housing 100.

As can be seen from the above description, one advantage of the dispensing system according to the present invention is that there is virtually no possibility of the front and rear bellows portions exhibiting hysteresis of spring characteristics since the front and rear bellows portions are never "locked" in a deformed state for an extended period of time. Accordingly, the dispensing system according to the present invention ensures that the discharged dosages do not substantially deviate from the calibrated dosage.

Another advantage of the dispensing system according to the present invention is that the actuation motion of the trigger 101 is perpendicular to the longitudinal axis of the dispensing system. Accordingly, there is little danger of accidental poking of the eyeball with the nozzle 2 since the motion to depress the trigger is not in the direction of the eye.

Yet another advantage of the dispensing system according to the present invention is that a single actuation motion of the trigger 101 enable the user to both load the drop cavity and subsequently discharge the precalibrated amount of medicament. The dispensing system according to the present invention is particularly useful for arthritic patients because the trigger mechanism allows for easy release of a medicament drop, thereby enabling more accurate delivery of the medicament drop to the eye. Furthermore, if the lower anterior section of housing 100 is equipped with a forwardly projecting finger 107, cul de sac of the eye, an area of low sensitivity and low tear turn over, may be specifically targeted by the present invention for application of medicament since the projecting finger 107 allows exposing of the cul de sac of the eye.

In the foregoing specification, the invention has been described with reference to specific exemplary embodiments thereof. It will, however, be evident that various modifications and changes may be made thereunto without departing from the broader spirit and scope of the invention as set forth in the appended claims. For example, the cartridge or housing may be adapted for use in conjunction with various types of vial-dispensers not specifically described herein, for example the vial-dispenser which is described in my U.S. Pat. 5,613,957 which has been expressly incorporated herein by reference. Furthermore, the spring action provided by flexible plastic material forming the front and rear bellows may be alternatively provided by a longitudinally disposed spring which urges the vial-dispenser to return to original position upon being released from the compressed state. In addition, although the vial-dispenser has been described in this specification as having an accordion-like front bellows portion and a rear bellows portion, the dispenser may alternatively incorporate any other spring configuration, e.g., a single spring element which is either integral with the dispenser body or separately formed. Furthermore, the specific arrangement of the trigger 101, the notched lever 102 and the wedge-shaped arm 103 may be modified, e.g., the trigger 101 and the notched lever 102 may be formed separately from one another and/or from the housing 100. The specification and drawings are accordingly to be regarded in an illustrative rather than a restrictive sense.

I claim:

1. A medicament-dispensing system comprising:

a vial for holding a volume of medicament;

a dispenser having an elastic, deformable body portion and a nozzle connected to said deformable body portion, said deformable body portion providing spring action and containing a dosage cavity, wherein said dispenser is actuated to load from said vial a calibrated amount of medicament into said cavity therein by deformation of said elastic, deformable body portion of the dispenser to a first non-ambient position and which is actuated to discharge said calibrated amount of medicament from said nozzle upon subsequent restoration of the deformable body portion to its ambient position;

a housing for retaining the dispenser, the housing having an anterior wall with an aperture for receiving the nozzle of the dispenser;

a one-way actuation release mechanism operationally coupled to said housing for actuating, by a single actuating motion, said dispenser to sequentially fill said cavity with medicament from said vial and subsequently discharge said medicament from said cavity through said nozzle, said one-way actuation release mechanism having a trigger and a release unit operationally coupled to said trigger and releasably engaging said deformable body portion, said release unit deforming said deformable body portion from said ambient position towards said first non-ambient position in a first phase of said actuating motion, said deformation causing flow of medicament from said vial to said cavity to fill said cavity, and said release unit disengaging from said deformable body portion at said first non-ambient position upon continuation of said actuating motion into a second phase, wherein said deformable body portion returns to said ambient position upon disengagement from said release unit to pressurize medicament in said cavity and discharge said medicament through said nozzle portion, and wherein said one-way actuation release mechanism facilitates substantially constant spring force of said deformable body portion over an extended period of time by preventing locking of said deformable body portion in any non-ambient position.

2. The medicament-dispensing system according to claim 1, wherein said release unit comprises a lever and a release arm, said lever being operationally coupled to said trigger and releasably engaging said deformable body portion when said deformable body portion is in said ambient position, and said release arm being positioned to oppose said lever at a predetermined position.

3. The medicament-dispensing system according to claim 2, wherein said lever is movable in concert with said deformable body portion in said first phase of said actuating motion, and wherein said release arm is internally positioned within the housing to oppose said lever when said deformable body portion is at said first non-ambient position so as to disengage said lever from said deformable body portion upon continuation of said actuating motion into said second phase.

4. The medicament-dispensing system according to claim 3, wherein said deformation of said deformable body portion occurs along its longitudinal axis.

5. The medicament-dispensing system according to claim 4, wherein said deformable body portion comprises an elastomeric material portion for providing spring action, and wherein said one-way actuation release mechanism substantially prevents creeping of said elastomeric material.

6. A system for dispensing medicament, which comprises:

a vial holding a volume of medicament;

an elastic, deformable body portion in fluid communication with said vial and containing a dosage cavity for collecting a predetermined volume of medicament from said vial, said deformable body portion having an integral elastomeric spring portion for providing spring action;

a nozzle portion connected to said deformable body portion for allowing discharge of said medicament collected in said dosage cavity;

a housing retaining said deformable body portion and said nozzle portion, said housing having an anterior wall with an aperture for receiving said nozzle portion; and a one-way release-actuation system having a trigger and a release mechanism, said release-actuation system actuating, by a single actuating motion of said trigger, said dispensing system to sequentially fill said dosage cavity with medicament from said vial and subsequently discharge said medicament from said dosage cavity, wherein said release mechanism engages and deforms at least said elastomeric spring portion of said deformable body portion in concert with a first phase of said actuating motion of said trigger, said deformation of said deformable body portion causing flow of medicament from said vial to said dosage cavity to fill said dosage cavity, and wherein said release mechanism disengages itself from said deformable body portion upon continuation of said actuating motion of said trigger into a second phase, said deformable body portion returning to said ambient position by action of said elastomeric spring portion upon disengagement from said release mechanism to pressurize medicament in said dosage cavity and discharge said medicament through said nozzle portion.

7. A one-way actuation release mechanism for actuating a medicament dispenser having an elastic, deformable body portion, which comprises:

a trigger; and a release unit operationally coupled to said trigger and adapted to releasably engage said deformable body portion, said release unit being adapted to deform said deformable body portion from an ambient position towards a first non-ambient position in a first phase of actuation to ready medicament for dispensation, and said release unit being adapted to disengage from said deformable body portion when said body portion has reached said first non-ambient position upon continuation of said actuation into a second phase;

wherein said one-way actuation release mechanism facilitates said deformable body portion to return to said ambient position upon disengagement from said release unit to discharge said medicament, and wherein said one-way actuation release mechanism facilitates substantially constant spring force of said deformable body portion over an extended period of time by preventing locking of said deformable body portion in any non-ambient position.

8. The one-way actuation release mechanism according to claim 7, wherein said release unit comprises a lever and a release arm, said lever being operationally coupled to said trigger and releasably engaging said deformable body portion when said body portion is in ambient position, and said release arm being positioned to oppose said lever at a predetermined position.

9. The one-way actuation release mechanism according to claim 8, wherein said lever is movable in concert with said deformable body portion in said first phase of actuation, and wherein said release arm is positioned to oppose said lever when said deformable body portion is at said first non-ambient position so as to disengage said lever from said deformable body portion upon continuation of said actuation into said second phase.

10. A method of dispensing medicament from a dispensing system having one-way actuation release mechanism, an elastic, deformable body portion and a dosage cavity therein, said one-way actuation release mechanism having a trigger and a release unit operationally coupled to said trigger and releasably engaging said deformable body portion, which method comprises:

deforming said deformable body portion from an ambient position towards a first non-ambient position by actuating said trigger through a first phase of an actuation motion to move a first component of said release unit releasably engaged to said deformable body portion, said deformation causing flow of medicament into said cavity to fill said cavity;

disengaging said first component of said release unit from said deformable body portion when said deformable body portion has reached said first non-ambient position upon continuation of said actuation motion into a second phase; and biasing said deformable body portion back toward said ambient position upon disengagement from said release unit to pressurize medicament in said cavity and discharge said medicament;

wherein said method facilitates maintenance of substantially constant spring force of said deformable body portion over an extended period of time by preventing locking of said deformable body portion in any non-ambient position.

11. The method according to claim 10, wherein said release unit comprises a release arm and a lever releasably engaging said deformable body portion, and wherein said step of disengaging said first component of said release unit from said deformable body portion at said first non-ambient position comprises opposingly engaging said release arm with said lever to disengage said lever from said deformable body portion.

* * * * *